United States Patent [19]

Vannice et al.

[11] 3,941,819

[45] Mar. 2, 1976

[54] CATALYTIC FORMATION OF HYDROCARBONS FROM CO HYDROGEN MIXTURES

[75] Inventors: M. Albert Vannice, Plainfield; Robert Lee Garten, Summit, both of N.J.

[73] Assignee: Exxon Research and Engineering Company, Linden, N.J.

[22] Filed: Dec. 30, 1974

[21] Appl. No.: 537,580

Related U.S. Application Data

[63] Continuation-in-part of Ser. No. 424,861, Dec. 13, 1973.

[52] U.S. Cl. .................. 260/449 R; 260/449 M
[51] Int. Cl.² ........................................ C07C 27/06
[58] Field of Search .................. 260/449 M, 449 R

[56] References Cited

FOREIGN PATENTS OR APPLICATIONS 1,271,098   6/1968   Germany ................ 260/449.6

OTHER PUBLICATIONS

Schultz et al., Bur. of Mines, Report of Investigations 6974 (1967), pp. 1–11.

*Primary Examiner*—Howard T. Mars
*Attorney, Agent, or Firm*—John Paul Corcoran

[57] ABSTRACT

A method for producing ethane, ethylene and dimethyl ether compounds, said method comprising the step of passing a mixture of CO and hydrogen over platinum supported on alumina at a temperature ranging from 100°C. to 400°C. and a pressure ranging from 1 to 100 atmospheres.

1 Claim, No Drawings

CATALYTIC FORMATION OF HYDROCARBONS FROM CO HYDROGEN MIXTURES

BACKGROUND OF THE INVENTION

This case is a Continuation-in-part of application bearing Ser. No. 424,861 filed on Dec. 13, 1973.

This invention pertains to improvements in the production of organic compounds from carbon monoxide and hydrogen. In one aspect, the invention relates to passing a feed stream containing hydrogen and carbon monoxide over a supported platinum catalyst.

Although a vast amount of research and development has been conducted over the past fifty years pertaining to the Fischer-Tropsch synthesis (the reaction between CO and $H_2$ to form organic compounds) almost no effort has been made to study the capability of noble metals to catalyze this reaction.

Although the metals of the platinum group are all generally active as hydrogenation-dehydrogenation catalysts, they differ considerably in their ability to catalyze the various reactions between carbon monoxide and hydrogen. Ruthenium has been known for many years to be an effective catalyst in the Fischer-Tropsch synthesis and in the catalytic synthesis of methane from carbon monoxide and hydrogen, the reactions producing high molecular weight waxes at high pressures and large quantities of methane at atmospheric pressure. Recently, suspensions of ruthenium oxides in a hydrocarbon solvent have been shown to possess exceptionally high activity, the CO-$H_2$ reaction being measurable at 100°C. By contrast, the other unsupported platinoid metals are much inferior catalysts for these reactions. Unsupported metals such as rhodium and osmium have been shown to exhibit some activity at elevated temperatures whereas platinum and iridium are generally inert for both the Fischer-Tropsch synthesis and the methanation reaction.

Of the nine Group VIII metals of interest, iron, cobalt and nickel have been heavily studied and large quantities of information exist in the literature. All three produce significant amounts of methane from a CO + $H_2$ feedstream but nickel is the most selective toward methane and is presently the commercially used catalyst for the methanation reaction.

In an article authored by F. Fischer, H. Tropsch and P. Dilthey, Brennstoff-Chemie 6, 265 (1925), the methanation activities of a series of unsupported metals were studied to determine the order of their activity. The metals were ruthenium, iridium, rhodium, nickel, cobalt, osmium, platinum, iron, molybdenum, palladium and silver. In addition to the fact that Fischer et al. never really defined their criteria for activity, none of these activities was corrected for differences in metal surface area. Surface area variations for the different metals could alter completely the order of activities of the metals. Platinum was not found to be one of the better catalysts. Platinum itself was studied over a temperature range of 20°-800°C. and no methane conversion was observed at 200°C. or lower and only small conversions were measured at 300°C.

In another article by H. Pichler, *Adv. in Catalysis* IV, 271 (1952), ruthenium was described as the most active catalyst for the low temperature, high-pressure synthesis of high molecular weight materials. It was verbally stated that ruthenium and osmium gave appreciable amounts of liquid and solid products but that platinum was "much less suitable" as a catalyst for this reaction. Palladium and iridium gave only traces of products.

In another article by McKee, D.W., J. Catal. 8, 240 (1967), the interaction of CO + $H_2$ at 1 atmosphere over various unsupported Group VIII metals was studied by the author. He found no evidence of methane formation over unsupported platinum even at temperatures exceeding 200°C. whereas rhodium and iridium produced small amounts of methane at 200°C. and supported ruthenium was quite active at 100°C.

Mills et al. "Catalysis Reviews" 8 (2) pages 199, 200 and 210 (1973) discloses that platinum supported on alumina is an interesting methanation catalyst. However, the subject inventors have found that if critical temperature and pressure conditions are observed that platinum on alumina can be employed to selectively produce ethane, ethylene and dimethyl ether compounds in addition to methane. Example 2 of the subject application will demonstrate that the Mills et al. article did not teach how to produce ethane, ethylene and dimethyl ether but was predominantly interested in producing methane.

However, if platinum is supported on alumina and critical temperature and pressure conditions are observed, it can be used to catalytically produce ethylene, ethane and dimethyl ether compounds from a mixture of CO and hydrogen. Supported platinum catalysts have several advantages over commercial nickel catalysts which include (1) better activity maintenance, (2) thermal stability (especially desirable for exothermic reactions such as CO + $H_2$ where temperature excursions may cause sintering of nickel catalysts, (3) better tolerance to sulfur, (4) better selectivity to methane, and (5) more tolerant to higher CO pressures and lower temperatures as platinum does not form volatile metal carbonyl as nickel would do under similar conditions.

Briefly, the subject invention relates to a method for producing ethylene, ethane and dimethyl ether, said method comprising the step of passing a mixture of CO and $H_2$ over platinum supported on alumina at a temperature and pressure sufficient to selectively form said organic compounds.

The catalyst used in accordance with this invention is formed by the steps of impregnating a suitable alumina support with a salt solution of the platinum followed by heat treating the impregnated support to form a chemical complex at the surface of the support and to drive off moisture.

Platinum may be added to the catalyst in the form of a solution containing a soluble platinum salt. Chloroplatinic acid ($H_2PtCl_6$), $Pt(NH_3)_4Cl_2$, $Pt(NH_3)_2(NO_2)_2$ or any other platinum salt which is soluble in the solvent used for the impregnation may be employed.

The impregnated support in powder or granular form is then treated by establishing time-temperature relationships suitable to produce a chemical change on the surface of the support and to remove water and adsorbed oxygen. Suitably, the impregnated support can be heated in air in an inert atmosphere or in vacuum, e.g., 20–29 inches of mercury, and from about 150°C. to about 650°C., preferably from about 200°C. to about 430°C. for periods ranging from about 0.5 to about 4 hours, or preferably from about 1 to about 2 hours. On the other hand, the reaction between the salt and support can be accomplished by the elevated temperatures while moisture is stripped from the support with nitrogen or other nonreactive gases. If desirable, the impregnation and heat treatihg steps can be conducted in multiple stages, for example, the support can be impregnated and then dried or partially dried at low temperature. Support can then be reimpregnated and again dried or partially dried. The heat treatment per se can also be conducted in multiple stages, if desired. The impregnated support, to facilitate handling, can thus be subjected to a first rather mild heat treatment to dry the support and thence in a second step, to a more severe treatment to produce the desired chemical change at the surface.

Suitable supports are the oxides in Groups II, III, IV, V and VI-B of the Periodic Chart of the Elements and are described in a Table found in the *Handbook of Chemistry and Physics*, Chemical Rubber Company, 45th ed. (1964) page B-2, though the oxides in Groups II, III-A and IV-A are preferred. Group III-A metal oxides, particularly alumina, are especially preferred. Alumina supports in fact are quite outstanding from a cost effect standpoint and are readily available. Silica-free alumina has been found especially suitable. Group II-A metal oxides such as magnesium oxide, calcium oxide, strontium oxide and barium oxide; also the Group IV metal oxides, e.g., titanium oxide and zirconium oxide; Group V metal oxides, e.g. vanadium oxide and activated carbon and coke are effective. Certain natural clays, diatomaceous earth, e.g. kieselguhr and other supports are also useful. Silicon dioxide and mixtures of silicon dioxide, aluminum oxide are also used in this invention as well as the zeolites. In fact, any refractory oxide that will give well-dispersed platinum is suitable in the use of this invention.

In order to selectively produce ethane and ethylene formation, platinum supported on alumina must be employed as the catalyst. The platinum loading ranges from 0.01 to 5 wt.% and preferably from 0.3 to 2 wt. % based on the total weight of the catalyst of the metal and the support. The hydrogen and CO mole ratio ranges from 0.1 to 5, the pressure ranges from 1 to 100 atmospheres, preferably from 1 to 20 atmospheres, and the temperature ranges from 100° to 400°C., preferably 200° to 300°C. Under these conditions the conversion to ethane and ethylene is approximately 5 – 15 mole %.

In order to increase the dimethyl ether formation, again the platinum-on-alumina is the catalyst that is employed. The platinum loading ranges from 0.01 to 5 wt. % and preferably from 0.3 to 2 wt. % based on the total weight of the catalyst. The hydrogen-to-CO mole ratio ranges from 0.1 to 2 and the pressure ranges from 2 to 100 atmospheres, preferably from 20 to 40 atmospheres and the temperature ranges from 100° to 400°C., preferably 200° to 300°C.

The specific activity of a catalyst is represented by a "Turnover Number", defined as the number of CO molecules reacted per second per site on the metal surface. The number is determined by selective chemisorption techniques using a gas such as carbon monoxide or hydrogen. Such gases are selectively chemisorbed on the metal surface and by employing justified, common assumptions such as 1 hydrogen atom adsorbs on every surface metal atom or 1 CO molecule adsorbs on every surface metal atom, the number of surface metal atoms, $M_s$, can be calculated. This value then represents the total number of metal surface sites and can also be used to calculate the metal dispersion, D, defined by $D = (M_s/M_t)$ where $M_t$ is the total number of metal atoms in the sample.

Such a representation of catalyst activity is very meaningful since it allows direct comparisons not only between different metals but also between different metal loadings of the same metal catalyst. Space velocity measurements do not correct for different metal loadings in different catalysts, or any differences in metal surface areas at the same loading, i.e., dispersion effects. If conversion data is desired, it is easily calculated from the following formula which assumes no diffusional limitations:

$$\text{Conversion} = \frac{\left(\text{Turnover Number} \frac{\text{molecules}}{\text{site-sec}}\right)(M_s)}{\left(\text{Reactant gas flow-}\frac{cc_{STP}}{\text{sec}}\right)\left(\frac{44.6 \ \mu\text{mole gas}}{1 \ cc \ \text{gas}}\right)\frac{6.02\times10^{17} \ \text{molecules}}{\mu\text{mole}}}$$

These supported platinum catalysts heretofore unrecognized as an active selective catalyst in the reaction between CO and hydrogen, are useful in any process producing such a mixture such as gasification of coal, residuum, oil shale, tar sands, etc. All these processes can utilize these catalysts to produce methane, or if desired, substantial quantities of ethane, ethylene and dimethyl ether using the reaction conditions specified hereinabove.

In order to describe the workings of the invention, the inventive process is described in the following illustrative examples.

Methods of catalyst preparation.

A. 1.75% Platinum on aluminum oxide

In a graduated cylinder 25 g of alumina with a surface area of 180 m²/g was soaked for 24 hours in 30 ml of chloroplatinic acid solution containing 0.455 g of platinum. At the end of 24 hrs, the original yellow chloroplatinic acid solution had become colorless and the platinum had been adsorbed on the alumina. The catalyst was then filtered and dried 16 hrs at 120°C. and 4 hrs at 260°C. in air.

B. 1.16% Platinum on Aluminum Oxide (prepared from p-salt)

A platinum on alumina catalyst free of chlorine was prepared from platinum p-salt [Pt(NH$_3$)$_2$(NO$_2$)$_2$]. A solution containing 0.116 g of platinum was prepared by dissolving 0.190 g of Pt(NH$_3$)$_2$(NO$_2$)$_2$ in 32.5 ml of distilled water at 90°–100°C. At the same time, 10 g of alumina was heated to 90°–100°C. and then 6.5 cc of hot Pt(NH$_3$)$_2$(NO$_2$)$_2$ solution was added to the hot alumina. The Pt(NH$_3$)$_2$(NO$_2$)$_2$ solution and the alumina were reheated and a second addition of 6.5 cc of solution was made. This procedure was continued until all the Pt(NH$_3$)$_2$(NO$_2$)$_2$ solution was added to the alumina. The catalyst was finally dried for 16 hrs at 120°C. and 4 hrs at 260°C. in air.

The catalyst prepared by this procedure B was used in the synthesis reactions described in Example 1 under the designated conditions.

TABLE 1

EXAMPLE-1
SYNTHESIS OF LIGHT HYDROCARBONS (Pt CATALYSTS)
(~ 1 atm)

| Catalyst | T (°C) | HC Formation (% CO Conv.) | Turnover No. Based on CO Ads. | $CO_2$ form. (% Co Conv.) | \multicolumn{6}{c}{HC Product Analysis, Mole %} | | | | | | $H_2$:CO Mole Ratio | Run No. | Metal Disp. D(%) CO | D(%) $H_2$ |
|---|---|---|---|---|---|---|---|---|---|---|---|---|---|---|---|
| | | | | | $C_1$ | $C_2$ | $C_2$= | $C_3$ | $C_4$ | $C_5$+ | $CH_3OCH_3$ | | | | |
| 1.16% Pt/$Al_2O_3$ (P-salt) | 271 | 0.44 | 0.0017 | 0.43 | 89 | 10 | 2 | — | — | — | tr | 1.0 | 92-3 | 37 | 71 |
| | 271 | 0.18 | 0.0014 | 0.15 | 82 | 7 | 12 | — | — | — | — | 0.5 | 92-4 | 37 | 71 |
| | 250 | 0.35 | — | 0.13 | 74 | 6 | 7 | tr | — | — | 12 | 1.2 | 91-5 | 37 | 71 |

EXAMPLE 2

The catalyst prepared by procedure A was used in the following synthesis reactions under the designated conditions.

| Run No. | Temp °C. | Pressure (ATM) | $H_2$/CO Ratio | % CO Conversion to Hydrocarbons | $N_{co}$ (sec$^{-1}$ ×10$^3$) | \multicolumn{5}{c}{Product Distribution (Mole %)} | | | | |
|---|---|---|---|---|---|---|---|---|---|---|
| | | | | | | $C_1$ | $C_2$= | $C_2$ | $C_3$+ | $CH_3$—O—C-$H_3$ |
| 1 | 263 | 1.96 | 1 | 0.7 | 2.9 | 89 | 2 | 10 | 0 | 0 |
| 2 | 262 | 1.35 | 1 | 1.5 | 2.0 | 86 | 1 | 14 | 0 | 0 |
| 3 | 247 | 1.99 | 1 | 0.8 | 3.0 | 85 | 4 | 11 | 0 | 0 |
| 4 | 271 | 2.12 | 1 | 0.8 | 5.4 | 85 | 2 | 8 | 0 | 5 |
| 5 | 274 | 10.10 | 1 | 2.5 | 13.3 | 70 | 1 | 7 | 0 | 23 |
| 6 | 272 | 21.12 | 1 | 2.9 | 18.1 | 67 | .5 | 5 | 0 | 25 |
| 7 | 270 | 2.10 | 1 | 0.1 | 0.7 | 100 | 0 | 0 | 0 | 0 |
| 8 | 269 | 21.00 | 1 | 0.9 | 8.8 | 69 | 0 | 4 | 0 | 27 |
| 9 | 269 | 30.00 | 1 | 0.7 | 6.0 | 67 | 0 | 4 | 0 | 30 |

This example definitely establishes that when the temperature and pressure are carefully controlled and the catalyst employed is platinum supported on alumina, that substantial amounts of ethylene and ethane are produced and that under higher pressures substantial amounts of dimethyl ether are also produced.

What is claimed is:

1. A process for producing substantial amounts of dimethyl ether, said process comprising the step of passing CO and $H_2$ over platinum supported on alumina, wherein the amount of platinum ranges from 0.3 to 2 wt. % based on total weight of the support including platinum at a temperature ranging from 200° to 300°C and a pressure ranging from 10.10 to 40 atmospheres and wherein the mol rato of hydrogen to CO ranges from 0.1 to 2.

* * * * *